(12) United States Patent
Howell

(10) Patent No.: US 6,228,060 B1
(45) Date of Patent: May 8, 2001

(54) BLOOD SEAL HAVING A SPRING-BIASED SEPTUM

(75) Inventor: Glade H. Howell, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/145,449

(22) Filed: Sep. 2, 1998

(51) Int. Cl.⁷ .................................................. A61M 5/178
(52) U.S. Cl. ............... 604/167.04; 604/256; 604/167.02; 604/167.01
(58) Field of Search .................... 604/256, 905, 604/167, 164, 158, 160, 161, 244, 284, 236, 264, 169, 537, 246, 167.02, 167.04, 167.03, 164.01, 164.02, 167.01

(56) References Cited

U.S. PATENT DOCUMENTS

| | | | |
|---|---|---|---|
| 4,314,555 | * 2/1982 | Sagae | 128/214.4 |
| 4,496,348 | * 1/1985 | Genese et al. | 604/167 |
| 5,211,634 | * 5/1993 | Vaillancourt | 604/167 |
| 5,409,461 | * 4/1995 | Steinman | 604/110 |
| 5,429,616 | * 7/1995 | Schaffer | 604/250 |
| 5,498,247 | 3/1996 | Brimhall | 604/244 |
| 5,531,810 | 7/1996 | Fullemann | 96/105 |
| 5,556,387 | * 9/1996 | Mollenauer et al. | 604/249 |
| 5,749,859 | * 5/1998 | Powell | 604/167 |

FOREIGN PATENT DOCUMENTS

| | | | |
|---|---|---|---|
| WO 96/23158 | 8/1996 | (WO) | F16L/37/28 |
| WO 98/23313 | 6/1998 | (WO) | A61M/5/00 |

* cited by examiner

Primary Examiner—Richard K. Seidel
Assistant Examiner—Cris Rodriguez
(74) Attorney, Agent, or Firm—Eric M. Lee, Esq.

(57) ABSTRACT

A blood seal having a spring-biased septum is provided for preventing the leakage of blood during the placement and use of vascular catheters and similar devices. The structure of the blood seal includes a housing with an internal channel. A spring-biased septum is placed securely within the channel such that it substantially blocks blood flow through the channel. The spring-biased septum includes an elastic plug having a pre-slit or pre-molded hole and a biasing element disposed about the elastic plug. A needle or other object may be withdrawn through the slit or hole, after which the biasing element forces the hole closed, preventing blood leakage.

11 Claims, 4 Drawing Sheets

BLOOD SEAL HAVING A SPRING-BIASED SEPTUM

BACKGROUND

1. The Field of the Invention

The present invention is related to a blood seal having a spring-biased septum for use in connection with various medical devices. More specifically, the present invention relates to a blood seal having a spring-biased septum which is particularly adaptable for use in sealing a vascular access device immediately following placement of a catheter into a blood vessel of a patient.

2. Technical Background

During medical treatment, patients often require medication, blood, or fluids. The most efficient way of administering these substances is by depositing them directly into a patient's blood stream where the circulatory system quickly directs the substance to the target tissue or organ. Thus, vascular catheters for infusion of fluids, blood, and medications into patients are among the most commonly used medical devices. The insertion of a vascular catheter allows repeated or continuous access to the circulatory system of a patient. Vascular catheters are generally inserted into the extremities of a patient and fluids, blood, and medications are introduced to the patient through such catheters.

Catheters of this type are generally inserted into a vein or artery by means of an introducer needle. In one common configuration, the catheter is initially placed over the needle. The needle, with the catheter located over the needle, is inserted into the patient until the desired vein or artery is located. Once the needle and catheter are properly located in the vein or artery, the needle is withdrawn from the catheter and discarded. The catheter remains in the vein or artery to provide access to the circulatory system of the patient without repeated needle punctures.

When the catheter insertion and placement steps have been concluded, one end of a tube (or "tubing set") is generally attached to the proximal end of the catheter. The opposite end of the tube is attached to a source of fluid and medication. The source of fluid is typically a bottle or bag containing the fluid required for treatment of the patient. Once attachment of the catheter to the fluid source is completed, fluids are allowed to flow through the tubing, into the catheter, and ultimately into the patient. In most situations, fluids flow through the tubing set and into the patient by means of gravity feed or using a standard infusion pump.

It will be appreciated that it is important to minimize the leakage of blood to the outside environment during each of the steps described above. Blood leakage can expose medical personnel and others to blood-borne diseases such as AIDS and hepatitis. Blood leakage can contaminate equipment and supplies in the treatment area. Blood leakage may also cause unnecessary alarm on the part of the patient and other observers. Thus, it is important to prevent or minimize blood leakage in order to maintain safety, aesthetics, and to retain equipment and supplies in good working order.

The placement and use of catheters of the type described above involve the potential for blood leakage. For example, the removal of the introducer needle once the catheter is in place generally results in a short period of time during which blood may flow out of the catheter to the surrounding environment.

Attempts have been made to deal with the problem of blood leakage during the placement of catheters. Many of these solutions employ latex or polyisoprene barriers that restrict blood flow. Such a barrier is situated so that after venipuncture and introduction of the catheter into the blood vessel of a patient, the introducer needle is withdrawn through the barrier or plug. Unfortunately, most polymers, including those used in blood barriers, tend to take a set over time, especially if an object such as a needle, wire, or cannula remains in the plug for a prolonged period before use. As a result, when the needle is withdrawn through the barrier, the hole left by the needle may fail to reseal, allowing blood to leak from the device.

Other attempts to deal with the problem of blood leakage typically involve devices that are expensive and complex to operate. For example, one such device employs a relatively complex valve mechanism connected to the proximal end of the catheter which opens when a needle is inserted and then closes when the needle is removed. The valve then opens again when the tubing set is attached to the catheter. This device requires a mechanism for repeated opening and closing of the valve, as well as other collateral structures which facilitate operation of the device. These relatively complex structures complicate the device and add to its cost. In addition, the valve device is designed to remain in place after the tubing set is attached. This increases the potential for irritation and discomfort to the patient. Such devices are also too expensive for wide use in developing countries, where the problem of HIV infection is growing and the need for cost-effective solutions is great.

Accordingly, it would be an advancement in the art to provide a device which would control the flow of blood during the steps surrounding placement and use of a catheter. It would also be an advancement in the art to provide such a device which is inexpensive and simple to operate. It would also be an advancement in the art to provide such a device which could be used without requiring significant modification of conventional catheters, needles, tubing sets and the like. Finally, it would be a significant advancement in the art to provide such a device which provided the medical professional with more control in performing the tasks surrounding placement and use of a catheter.

Such apparatus are disclosed and claimed herein.

BRIEF SUMMARY AND OBJECTS OF THE INVENTION

The present invention is a blood seal having a spring-biased septum for preventing the leakage of blood during the placement and use of vascular catheters and similar devices. In one presently preferred embodiment, the blood seal has a housing, at least part of which is substantially cylindrical in configuration. An internal channel through the housing is provided. A spring-biased septum is disposed within and substantially blocks the internal channel. In certain preferred embodiments, the spring-biased septum includes a formed elastic plug with a pre-slit or pre-molded hole. In certain preferred embodiments, the elastic plug may be formed of a biocompatible elastomer such as latex or polyisoprene.

In certain preferred embodiments, the elastic plug includes an annular groove in which a biasing element sits. The biasing element is disposed about the elastic plug and keeps the slit or hole closed with a predictable force. In certain preferred embodiments of the present invention, the biasing element is a C-shaped spring constructed of a metal or metal alloy. In certain especially preferred embodiments, the biasing element is a C-shaped spring constructed of spring steel.

It will be appreciated that the biasing element prevents blood flow through the hole or slit, while the elastic plug prevents blood from flowing around the spring-biased septum. In certain embodiments, the housing may be constructed of a soft elastomer. In such embodiments, the spring 20 biased septum may optionally include a rigid plug retainer that surrounds and radially compresses at least part of the length of the elastic plug, thereby preventing leakage between the plug and the housing. In other embodiments, the housing is constructed of more rigid material, eliminating the need for a rigid plug retainer.

In certain preferred embodiments, the blood seal housing is attached to the catheter during the catheter placement steps. In such embodiments, the housing forms a portion of a connector to which syringes and tubing sets may be attached. In other preferred embodiments, the blood seal housing is distinct from but attached to a connector.

The blood seal of the present invention provides a self-closing seal through which an object such as a needle, wire, or cannula may be moved. In certain preferred embodiments, the blood seal allows removal of an introducer needle from a vascular access device. In such embodiments, a portion of the introducer needle is disposed within the slit or hole in the elastic plug. After venipuncture and the introduction of the catheter into the patient's blood vessel, the user withdraws the needle through the blood seal by pulling on a finger grip. After the needle is withdrawn, the biasing element squeezes the elastic plug, closing the hole or slit.

In other preferred embodiments, the introducer needle is attached to a wire, a portion of which is disposed within the slit or hole in the elastic plug. After proper placement of the catheter, the user withdraws the wire and the needle through the blood seal by pulling a finger grip. As described above, the biasing element forces the hole or slit closed after withdrawal of the wire and needle.

From the foregoing, it will be appreciated that a spring-biased septum may be used anytime a needle, cannula, wire, or other similar object must pass through a seal. The present invention is especially useful in controlling blood leakage during the placement and use of vascular catheters. Thus, the problems related to blood leakage to the ambient environment are substantially reduced.

The present invention also provides a device that is simple and inexpensive to operate, and may be used without significant modification of conventional catheters and tubing sets.

These and other objects and advantages of the invention will become apparent upon reading the following detailed description and appended claims, and upon reference to the accompanying drawings.

BRIEF DESCRIPTION OF THE DRAWINGS

In order to more fully understand the manner in which the above-recited advantages and objects of the invention are obtained, a more particular description of the invention briefly described above will be rendered by reference to specific embodiments thereof which are illustrated in the appended drawings. Please take note that the embodiments illustrated in the drawings are merely illustrative.

DETAILED DESCRIPTION OF THE PREFERRED EMBODIMENTS

The present invention can be best understood by reference to the drawings where like parts are designated with like numerals throughout. One embodiment of a vascular access device incorporating the blood seal having a spring-biased septum of the present invention is generally designated 10 in FIG. 1. As mentioned above, the vascular access device 10 allows for the placement of a catheter in a patient and subsequent removal of the introducer needle while maintaining a blood seal at the proximal end of the catheter. This allows a medical professional to introduce a catheter into a patient's blood vessel and remove the introducer needle without the need to be concerned about blood leakage.

Figure 1:
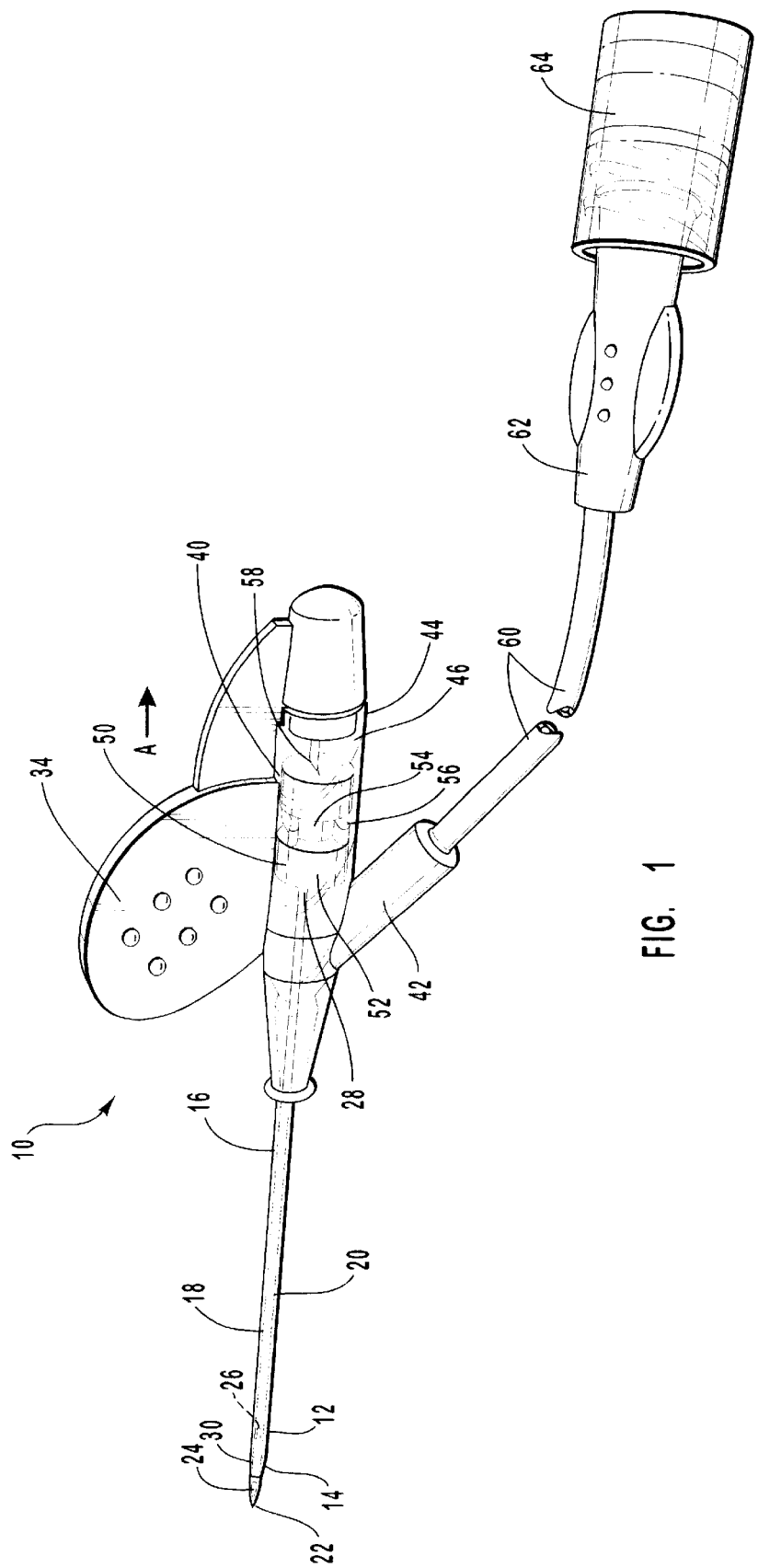
FIG. 1 is a perspective view of one embodiment of a vascular access device incorporating the blood seal having a spring-biased septum of the present invention.

As illustrated in FIG. 1, the vascular access device 10 includes a catheter 12. The catheter 12 has a distal end 14, a proximal end 16, and an internal lumen 18. A needle 20 having a sharpened end 22 is slidably mounted within the internal lumen 18 of the catheter 12, such that the sharpened end 22 of the needle protrudes a short distance beyond the distal end 14 of the catheter 12. The sharpened end 22 allows a medical professional to puncture the blood vessel of a patient, creating an access site and facilitating the introduction of the distal end 14 of the catheter 12 into the blood vessel. The distal end 14 of the catheter 12 is tapered, allowing dilation of the access site as the distal end 14 of the catheter 12 is introduced into the blood vessel.

The needle includes a distal opening 24, a notch-like opening 26, and a lumen 30. The lumen permits fluid to flow between the distal opening 24 and the notch-like opening 26.

The needle is provided with a proximal end 28 attached to a finger grip 34. The needle 20 extends coaxially through the internal lumen 18 of the catheter, passes through a blood seal 40 disposed within a branched connector 42, and is attached to the finger grip 34, such that after the introduction of at least part of the catheter 12 into the blood vessel, the needle 20 may be withdrawn from the access site by pulling the finger grip 34 in the direction indicated by arrow A, the risk of injury to the blood vessel.

The branched connector 42 includes a housing 44 and an internal channel 46 through the housing 44. Disposed within and substantially blocking the internal channel 46 is a spring-biased septum 50. The housing 44, internal channel 46, and spring-biased septum 50 form a blood seal.

Figure 2:
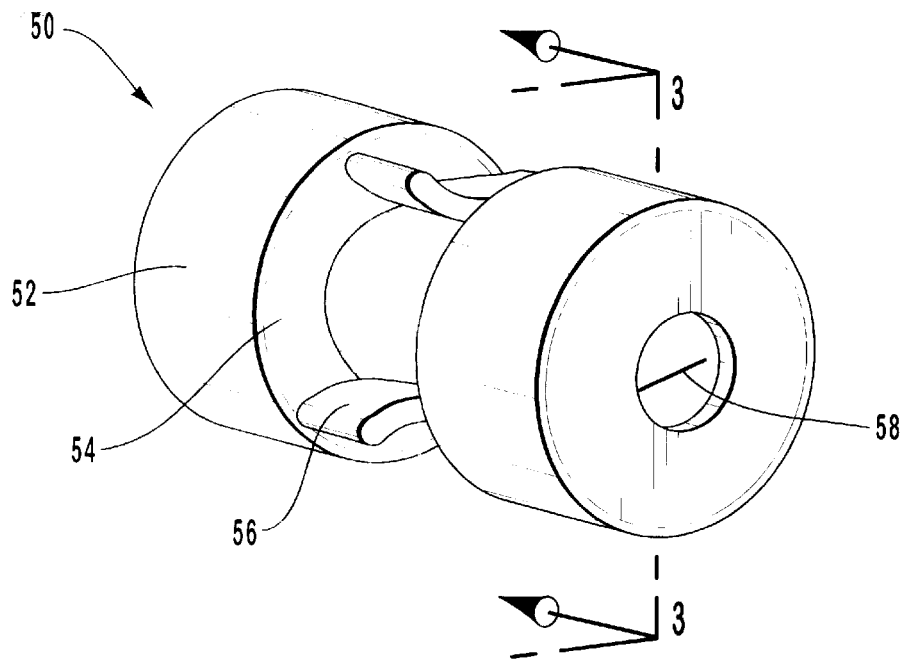
FIG. 2 is a perspective view of the spring-biased septum after the needle has been withdrawn.

FIG. 2 shows a perspective view of the spring-biased septum 50, which includes a dumbbell shaped elastic plug 52. The elastic plug 52 may be constructed of a biocompatible elastomer. In certain preferred embodiments, the elastic plug 52 is constructed of polyisoprene or latex. The elastic plug 52 has an annular groove 54 in which a biasing element 56 is disposed. In the embodiment shown in FIGS. 1 and 2, the biasing element 56 is a C-shaped spring. The biasing element 56 may be constructed of a resilient material. In certain preferred embodiments, the biasing element 56 is constructed of a metal or a metal alloy. The biasing element 56 may, for example, be constructed of spring steel.

The elastic plug 52 also includes a slit 58 through which the needle 20 passes. It will be appreciated that the slit 58 may be replaced by any of a number of equivalent elements, such as a hole or channel through the elastic plug 52. Prior to use, a portion of the needle 20 is disposed within the slit 58. After the needle 20 is withdrawn, the slit 58 closes to prevent blood leakage.

Figure 3:
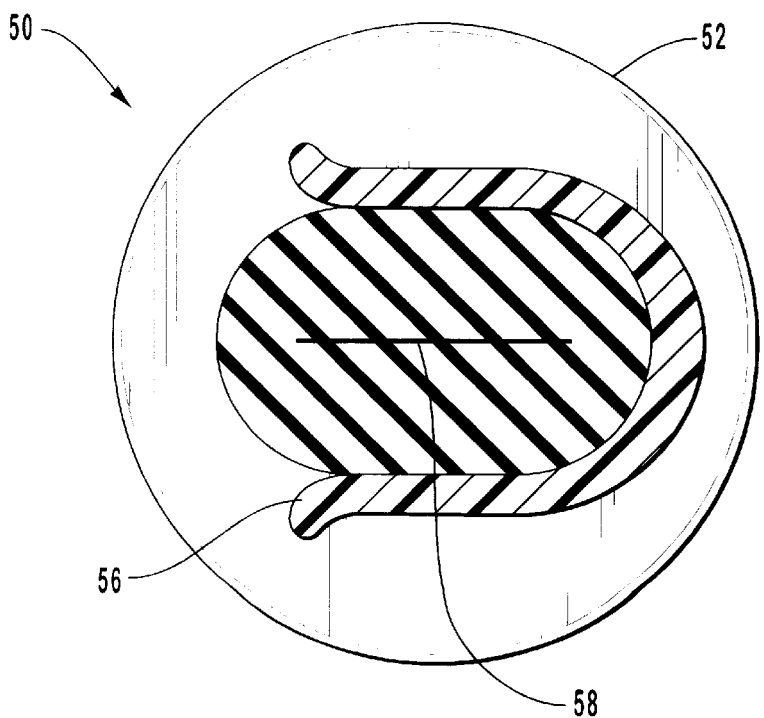
FIG. 3 is a cross-sectional view taken along line 3—3 of FIG. 2.

FIG. 3 shows a cross sectional view of the spring-biased septum 50 after the needle has been withdrawn. The elastic plug 52, biasing element 56, and slit 58 are illustrated. From this view, it will be appreciated that the biasing element 56 compresses a portion of the elastic plug 52, keeping the slit 58 closed with a predictable force.

Figure 4:
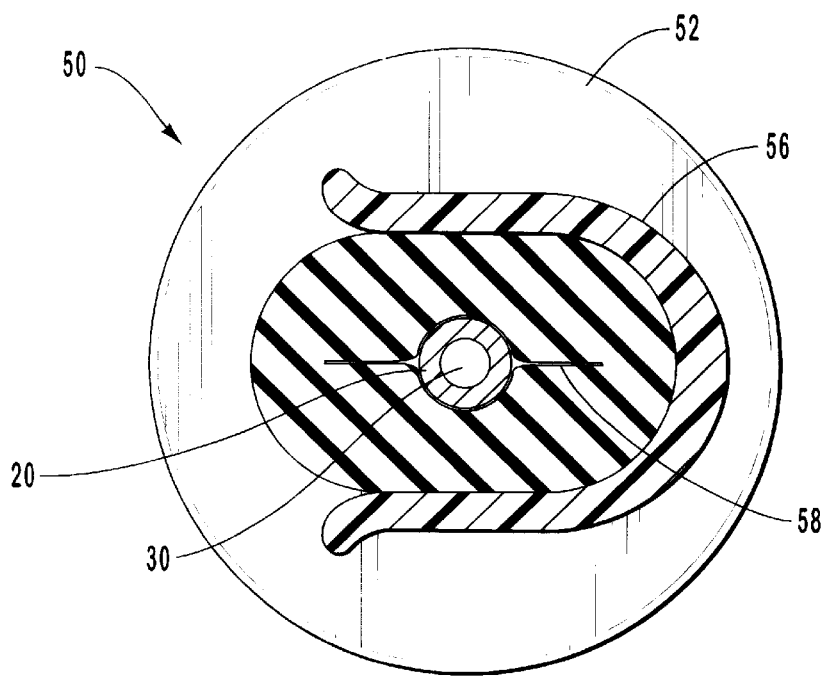
FIG. 4 is a cross-sectional view of the spring-biased septum prior to removal of the needle.

FIG. 4 shows a cross-sectional view of the spring-biased septum 50 prior to removal of the needle 20. The needle 20, elastic plug 52, biasing element 56, and slit 58 are illustrated. This Figure illustrates the manner in which the needle 20 penetrates the spring-biased septum 50 through the slit 58.

Figure 5:
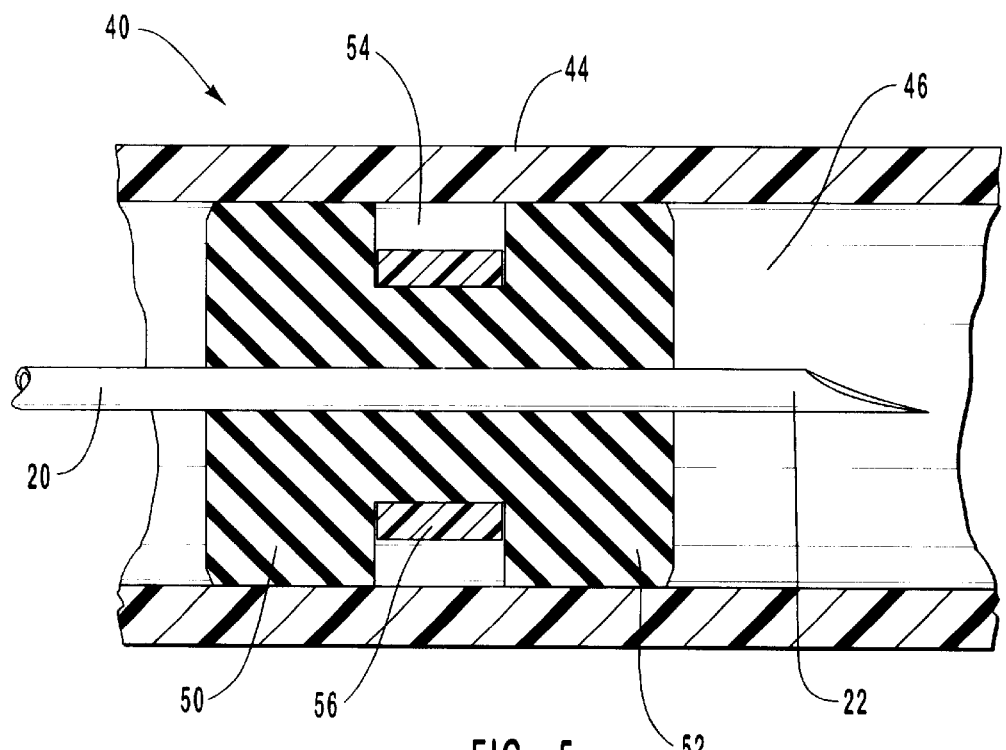
FIG. 5 is a longitudinal cross-sectional view of the blood seal prior to removal of the needle.

FIG. 5 shows a longitudinal cross-sectional view of the blood seal 40 prior to withdrawal of the needle 20 through the spring-biased septum 50. The housing 44, internal channel 46, and spring-biased septum 50, which includes the elastic plug 52, the annular groove 54, and the biasing element 56 are illustrated.

Returning to FIG. 1, the vascular access device 10 includes means for attaching conventional tubing sets and syringes. The branched connector 42 is attached to a tube 60, which is attached to a female adaptor 62. The female adaptor 62 permits removable attachment of syringes or other connectors. The embodiment of the vascular access device 10 shown in FIG. 1 also includes an injection piece 64 attached to the female adaptor 62. When the distal end 14 of the catheter 12 is in the blood vessel of a patient, medications may be injected via the injection piece 64. It will be appreciated that other attachment means, such as threaded connectors and luer locks, are well known in the art and may be used with the present invention.

In operation, the user grips the vascular access device 10 by the branched connector 42 (shown in FIG. 1) and punctures the blood vessel of a patient with the sharpened end 22 of the needle 20, facilitating the introduction of at least part of the distal end 14 of the catheter 12 into the patient's blood vessel. The notch-like opening 26 allows the user to monitor the placement of the needle 20. Blood flashback through the distal opening 24, into the lumen 30 of the needle 20, and out the notch-like opening 26 verifies blood vessel puncture.

After proper placement of the needle 20 and the distal end 14 of the catheter 12 into the patient's blood vessel the needle 20 is withdrawn to prevent inadvertent damage to the blood vessel. The user withdraws the needle 20 by pulling on the finger grip 34, which is attached to the proximal end 28 of the needle 20, in the direction of arrow A. The sharp tip 22 of the needle 20 is withdrawn through the spring-biased septum 50. The biasing element 56 forces the slit 58 to close, preventing blood leakage. The user may then discard needle 20, which is still attached to finger grip 34, in a container designed for disposal of blood-contaminated sharps or as otherwise might be appropriate.

Removal of the needle 20 leaves the distal end 14 of the catheter 12 in the patient's blood vessel. The user may then introduce a source of fluids or inject medications via the female adaptor or injection piece 64. The means of connecting sources of fluids and medications to the types of connector shown are well known in the art. Fluids and medications flow into the tube 60, through the branched connector 42 and catheter 12, and into the blood vessel of the patient.

Figure 6:
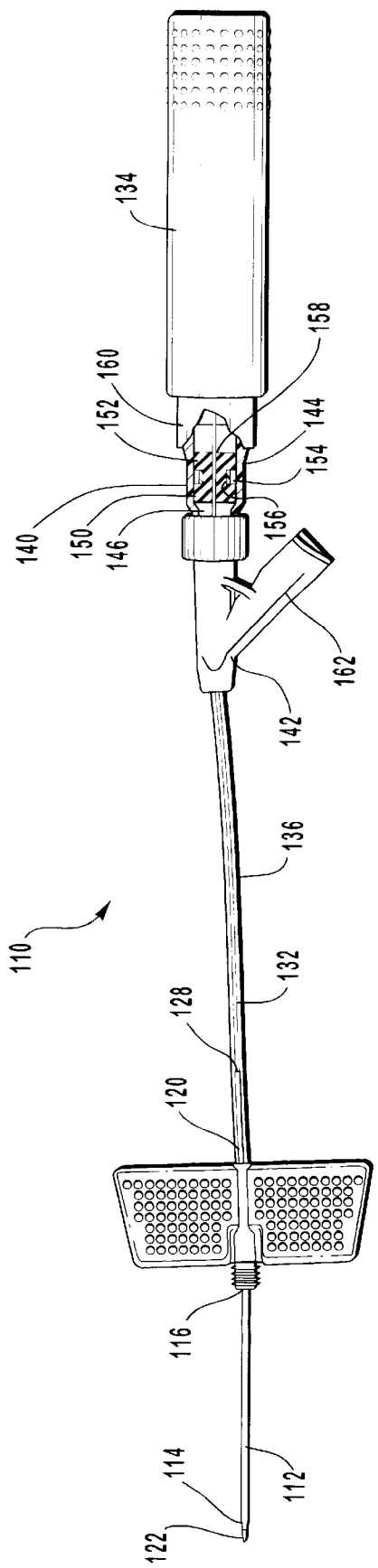
FIG. 6 is a partially cut-away plan view of a second embodiment of a vascular access device incorporating the blood seal having a spring-biased septum of the present invention.

A second embodiment of a vascular access device incorporating the spring-biased septum of the present invention is generally designated 110 in FIG. 6. The vascular access device 110 includes a catheter 112 having a distal end 114 and a proximal end 116. A needle 120 having a sharpened end 122 is slidably mounted within the catheter 112, such that the sharpened end 122 of the needle protrudes a short distance beyond the distal end 114 of the catheter 112. It will be appreciated that the needle 120 may incorporate openings as described above that permit the user to monitor placement of the needle 120. The sharpened end 122 allows a medical professional to puncture the blood vessel of a patient, creating an access site and facilitating the introduction of the distal end 114 of the catheter 112 into the blood vessel. The distal end 114 of the catheter 112 is tapered, allowing dilation of the access site as the distal end 114 of the catheter 112 is introduced into the blood vessel.

The needle 120 is provided with a proximal end 128 attached to a wire 132. At the opposite end of the wire 132 from the proximal end 128 of the needle 120 is a finger grip 134, such that after the introduction of at least part of the catheter 112 into the blood vessel, the needle 120 may be withdrawn from the access site by pulling the finger grip 134, minimizing the risk of injury to the blood vessel. The needle is withdrawn through a tube 136 and a branched connector 142, through a blood seal 140, and into a protective sheath 160. The protective sheath 160 may be as described in U.S. Pat. No. 5,304,136 and functions to protect the user from an inadvertent needle stick.

The blood seal 140 includes a housing 144 and an internal channel 146. A spring-biased septum 150 is disposed within and substantially blocks the internal channel 146. The spring-biased septum 150 is formed as described above and includes an elastic plug 152 with an annular groove 154. A biasing element 156 is disposed within the annular groove 154. The elastic plug includes a slit 158. Prior to use, a portion of the wire 132 is disposed within the slit 158. After placement of a portion of the catheter 112 into the blood vessel of the patient, the wire 132 and needle 120 are withdrawn through the slit 158. The biasing element 156 compresses a portion of the elastic plug 152, closing the slit 158 and preventing blood leakage.

The vascular access device 110 includes means for attaching conventional tubing sets and syringes. The branched connector 142 includes a female adaptor 162, permitting removable attachment of syringes of other connectors. It will be appreciated that other attachment means, such as threaded connectors and luer locks, are well known in the art and may be used with the present invention.

In operation, the user punctures the blood vessel of a patient with the sharpened end 122 of the needle 120, facilitating the introduction of at least part of the distal end 114 of the catheter 112 into the patient's blood vessel. After proper placement of the needle 120 and the distal end 114 of the catheter 112 the needle 120 is withdrawn to prevent inadvertent damage to the blood vessel. The user withdraws the needle 120 by pulling on the finger grip 134, which is attached to the wire 132, which, in turn, is attached to the proximal end 128 of the needle 120. The needle 120 is withdrawn from the catheter 112, through the tube 136 and branched connector 142, through the blood seal 140, and into the protective sheath 160. The user may then discard the protective sheath 160.

Removal of the needle 120 leaves the distal end 114 of the catheter 112 in the patient's blood vessel. The user may then introduce a source of fluids or inject medications via the female adaptor 162. Fluids and medications flow through the branched connector 142, tube 136, and catheter 112 and into the blood vessel of the patient.

In summary, the present invention provides a device which controls the flow of blood during the steps involved in the insertion of a catheter. The present invention provides a device which is inexpensive and simple to operate. The blood seal of the present invention can also be used without significant modification of conventional catheters, needles, tubing sets and the like.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by Letters Patent is:

1. A spring-biased septum comprising:

an elastic plug comprising an annular groove;

a slit disposed longitudinally through the elastic plug; and a biasing element contacting said plug and disposed within the annular groove of the elastic plug such that the biasing element substantially closes the slit to fluid leakage.

2. A spring-biased septum as defined in claim 1, wherein the elastic plug is constructed of a biocompatible elastomer.

3. A spring-biased septum as defined in claim 1, wherein the biasing element comprises a C-shaped spring.

4. A spring-biased septum as defined in claim 3, wherein the C-shaped spring is constructed of a metal or a metal alloy.

5. A spring-biased septum as defined in claim 3, wherein the C-shaped spring is constructed of spring steel.

6. A spring-based septum as defined in claim 1, wherein the elastic plug is constructed of latex or polyisoprene.

7. A blood seal comprising:

a housing:

an internal channel disposed through the housing;

an elastic plug having an outer circumference and disposed within and substantially blocking the internal channel wherein the elastic plug further comprises an annular groove disposed in an outer surface of the plug;

a slit disposed longitudinally through the elastic plug; and a biasing element contacting the outer circumference of the elastic plug and disposed within the housing such that the biasing element substantially closes the slit to fluid leakage.

8. A blood seal as defined in claim 7, further comprising a needle disposed longitudinally within the internal channel such that at least a portion of the needle passes through the hole in the elastic plug.

9. A blood seal as defined in claim 7, further comprising a wire disposed longitudinally within the internal channel such that at least a portion of the wire passes through the hole in the elastic plug.

10. A blood seal as defined in claim 9, wherein the wire is attached to a needle.

11. A blood seal as defined in claim 7, further comprising a rigid plug retainer disposed within the internal channel such that the rigid plug retainer surrounds and radially compresses at least part of a length of the elastic plug.

\* \* \* \* \*